(12) United States Patent
Pugh

(10) Patent No.: US 9,185,486 B2
(45) Date of Patent: Nov. 10, 2015

(54) OPHTHALMIC LENS WITH MICRO-ACOUSTIC ELEMENTS

(71) Applicant: Johnson & Johnson Vision Care, Inc., Jacksonville, FL (US)

(72) Inventor: Randall Braxton Pugh, St. Johns, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 66 days.

(21) Appl. No.: 14/011,230

(22) Filed: Aug. 27, 2013

(65) Prior Publication Data

US 2015/0063605 A1    Mar. 5, 2015

(51) Int. Cl.
| | |
|---|---|
| *H04R 25/00* | (2006.01) |
| *H04R 1/46* | (2006.01) |
| *A61F 2/16* | (2006.01) |
| *G02C 11/00* | (2006.01) |
| *G02C 7/04* | (2006.01) |
| *G06F 19/00* | (2011.01) |

(52) U.S. Cl.
CPC .. *H04R 1/46* (2013.01); *A61F 2/16* (2013.01); *G02C 7/04* (2013.01); *G02C 11/10* (2013.01); *G06F 19/3418* (2013.01); *H04R 25/606* (2013.01)

(58) Field of Classification Search
USPC ........................................................ 381/326
See application file for complete search history.

(56) References Cited

U.S. PATENT DOCUMENTS

| | | | | |
|---|---|---|---|---|
| 5,251,627 | A * | 10/1993 | Morris | 600/398 |
| 7,631,968 | B1 | 12/2009 | Dobson et al. | |
| 2008/0130867 | A1 * | 6/2008 | Bowen | 379/443 |
| 2010/0067723 | A1 * | 3/2010 | Bergmann et al. | 381/315 |
| 2010/0103369 | A1 | 4/2010 | Pugh et al. | |
| 2010/0142740 | A1 * | 6/2010 | Roerup | 381/330 |
| 2011/0158444 | A1 * | 6/2011 | Waldmann | 381/326 |
| 2012/0199995 | A1 | 8/2012 | Pugh | |
| 2012/0242953 | A1 | 9/2012 | Pugh et al. | |

FOREIGN PATENT DOCUMENTS

WO    WO 2010051203 A1    5/2010

OTHER PUBLICATIONS

PCT International Search Report for PCT/US2014/052486 Date of Completion Oct. 29, 2014 Date of Mailing Nov. 19 2014.

* cited by examiner

*Primary Examiner* — Davetta W Goins
*Assistant Examiner* — Amir Etesam

(57) ABSTRACT

The present invention discloses an ophthalmic device with micro-acoustic electromechanical elements and associated methods. In some embodiments, the micro-acoustic electromechanical elements may be useful for the purpose of providing audible warnings and/or messages to a user. The audible warnings and/or messages can include, for example, messages transmitted wirelessly through a communication element of the ophthalmic device and/or generated within the ophthalmic device. In addition, in some embodiments the ophthalmic device can be an energized contact lens that is used both for optical correction and the transmission of sound through bone resonance to the inner ear of a user.

20 Claims, 7 Drawing Sheets

OPHTHALMIC LENS WITH MICRO-ACOUSTIC ELEMENTS

FIELD OF THE INVENTION

This invention describes an energized Ophthalmic Device with micro-acoustic elements, and more specifically, the micro-acoustic elements forming part of the Ophthalmic Device and being capable of transmitting sound through bone resonance to the inner ear.

BACKGROUND OF THE INVENTION

Traditionally, an ophthalmic device, such as a contact lens, an intraocular lens, or a punctal plug, included a biocompatible device with a corrective, cosmetic, or therapeutic quality. A contact lens, for example, may provide one or more of vision correcting functionality, cosmetic enhancement, and therapeutic effects. Each function is provided by a physical characteristic of the lens. A design incorporating a refractive quality into a lens may provide a vision corrective function. A pigment incorporated into the lens may provide a cosmetic enhancement. An active agent incorporated into a lens may provide a therapeutic functionality. Such physical characteristics are accomplished without the lens entering into an energized state. An ophthalmic device has traditionally been a passive device.

Novel ophthalmic devices based on energized ophthalmic inserts have recently been described. These devices may use the energization function to power active optical components. For example, a wearable lens may incorporate a lens assembly having an electronically adjustable focus to augment or enhance performance of the eye.

Moreover, as electronic devices continue to be miniaturized, it is becoming increasingly more likely to create wearable or embeddable microelectronic devices for a variety of uses. For example, in one unrelated field, bone conduction of sound to the inner ear has been explored in headphones, hearing aids, and underwater communication products for diverse purposes. Amongst those purposes, the function of sound through bone conduction has been explored to enhance sound to individuals with normal hearing and/or provide sound to individuals with impaired hearing. However, these have been independent sound devices with limited functionality and typically include various mounting means, usually large and impractical, to allow for their use. As a result, new devices that can implement sound through bone conduction are desired.

SUMMARY OF THE INVENTION

The foregoing needs are met, to a great extent, by the present invention, wherein in one aspect an energized Ophthalmic Device incorporating micro-acoustic elements is disclosed. The micro-acoustic elements of the Ophthalmic Device which can be used to send sound to the inner ear using frequencies that can be conducted through the bones in the skull.

According to some aspects of the disclosure, an ophthalmic device including an energy source, a microprocessor in communication with and energized by the energy source, and a micro-electromechanical transducer also energized by the energy source and in electrical communication with the microprocessor, wherein the processor is configured to convert electrical signals into mechanical vibrations for the micro-electromechanical transducer to play an audible signal to a user of the ophthalmic device is disclosed. In some embodiments, the ophthalmic device may be a hydrogel contact lens configured to provide vision correction and/or enhancement and sound. Further, an antenna configured to provide a wireless communication between the microprocessor of the ophthalmic device and a wireless device may also be included. The antenna is configured to receive an RF signal used to energize the ophthalmic device and/or for one or more of: a smart phone, a tablet, a personal computer, a MP3 player, a medicinal pump, and a personal digital assistant to communicate with the ophthalmic device.

In additional aspects of the disclosure, a method of transmitting an audible signal to a user includes: generating signal data using one or more sensor(s) forming part of an ophthalmic device, transmitting said generated signal data to a processor, and converting, using the processor and a micro-electromechanical transducer forming part of the ophthalmic device, said transmitted signal into an audible signal for the user of the ophthalmic device.

In yet additional aspects of the disclosure, a method of transmitting an audible signal to a user can include: receiving digital data through a wireless communication element of an energized ophthalmic device, and converting said signal data transmitted through the wireless communication element into mechanical vibrations producing an audible signal using a processor and a micro-electromechanical transducer forming part of the energized ophthalmic device.

BRIEF DESCRIPTION OF THE DRAWINGS

The foregoing and other features and advantages of the invention will be apparent from the following, more particular description of preferred embodiments of the invention, as illustrated in the accompanying drawings.

DETAILED DESCRIPTION OF THE INVENTION

Figure 1:
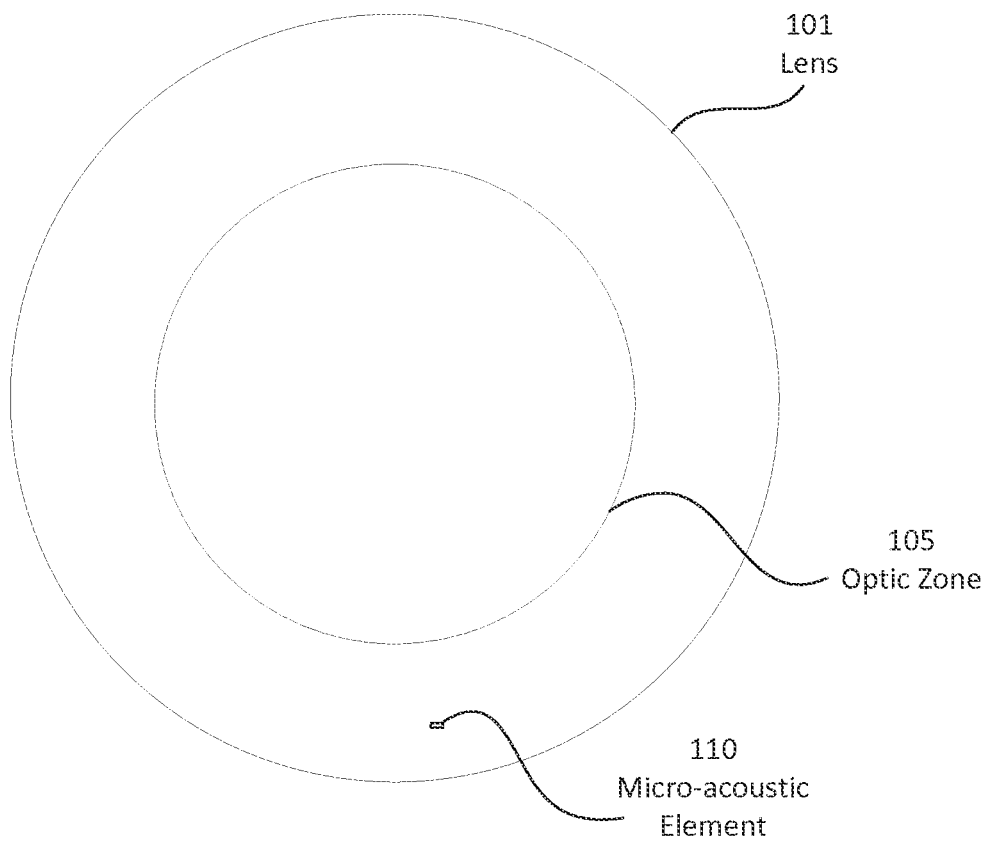
FIG. 1 is a diagrammatic representation of a first exemplary energized ophthalmic device comprising both optics and a micro acoustic electromechanical system in accordance with aspects of the present disclosure.

The disclosure will now be described with reference to the drawing figures, in which like reference numerals refer to like parts throughout.

Various aspects of the ophthalmic device and method disclosed may be illustrated by describing components that are coupled, sealed, attached, and/or joined together. As used herein, the terms "coupled", "sealed", "attached", and/or "joined" are used to indicate either a direct connection between two components or, where appropriate, an indirect connection to one another through intervening or intermediate components. In contrast, when a component is referred to as being "directly coupled", "directly sealed", "directly attached", and/or "directly joined" to another component, there are no intervening elements present.

Relative terms such as "lower" or "bottom" and "upper" or "top" may be used herein to describe one element's relationship to another element illustrated in the drawings. It will be understood that relative terms are intended to encompass different orientations in addition to the orientation depicted in the drawings. By way of example, if aspects of an exemplary ophthalmic device shown in the drawings are turned over, elements described as being on the "bottom" side of the other elements would then be oriented on the "top" side of the other elements. The term "bottom" can therefore encompass both an orientation of "bottom" and "top" depending on the particular orientation of the apparatus.

Various aspects of an ophthalmic device with Micro-Acoustic Elements may be illustrated with reference to one or more exemplary embodiments. As used herein, the term "exemplary" means "serving as an example, instance, or illustration," and should not necessarily be construed as preferred or advantageous over other embodiments disclosed herein.

Glossary

In this description and claims directed to the disclosed invention, various terms may be used for which the following definitions will apply:

Energized: as used herein refers to the state of being able to supply electrical current to or to have electrical energy stored within.

Energy: as used herein refers to the capacity of a physical system to do work. Many uses within this disclosure may relate to the said capacity being able to perform electrical actions in doing work.

Energy Source: as used herein refers to a device or layer that is capable of supplying Energy or placing a logical or electrical device in an Energized state.

Energy Harvester: as used herein refers to a device capable of extracting energy from the environment and converting it to electrical energy.

Functionalized: as used herein refers to making a layer or device able to perform a function including for example, energization, activation, or control.

Leakage: as used herein refers to unwanted loss of energy.

Ophthalmic Device: as used herein refers to any device that resides in or on the eye. These devices may provide optical correction, may be cosmetic, or may provide functionality unrelated to the eye. For example, the term lens may refer to a contact lens, intraocular lens, overlay lens, ocular insert, optical insert, or other similar device through which vision is corrected or modified, or through which eye physiology is cosmetically enhanced (e.g. iris color) without impeding vision. Alternatively, the Lens may provide non-optic functions such as, for example, monitoring glucose, delivering sound signals and/or administrating medicine. In some embodiments, the preferred lenses of the invention are soft contact lenses are made from silicone elastomers or hydrogels, which include, for example, silicone hydrogels, and fluorohydrogels.

Lithium Ion Cell: as used herein refers to an electrochemical cell where Lithium ions move through the cell to generate electrical energy. This electrochemical cell, typically called a battery, may be reenergized or recharged in its typical forms.

Media Insert: as used herein refers to an encapsulated insert that will be included in an energized ophthalmic device. The energization elements and circuitry may be incorporated in the Media Insert. The Media Insert defines the primary purpose of the energized ophthalmic device. For example, in embodiments where the energized ophthalmic device allows the user to adjust the optic power, the Media Insert may include energization elements that control a liquid meniscus portion in the Optical Zone. Alternatively, a Media Insert may be annular so that the Optical Zone is void of material. In such embodiments, the energized function of the Lens may not be optic quality but may be, for example, monitoring glucose, sound delivery, and/or administering medicine.

Micro-Acoustic Element(s): as used herein can refer to a micro acoustic electromechanical system and/or related components that can be used to conduct audible frequencies from the orb of the eye to the inner ear through the bones in the skull. In some embodiments, the micro-acoustic elements can include, for example, a microelectro-mechanical (MEMS) piezoelectric acoustic transducer and/or a condenser acoustic device, Energized by an Energy Source.

Microfluidic Analytical Systems: as used herein can refer to a low energy consumption system including one or more pore(s) from which a fluid sample may be collected from, and in some embodiments, moved through a channel or diffused, for the characterization of one or more properties of the fluid sample. In some embodiments, the Microfluidic Analytical Systems can include active microfluidic components, such as micro-pumps and micro-valves. Alternatively or additionally, in some embodiments, droplets may be controlled, for example, using electrowetting and/or electrophoresis techniques.

Operating Mode: as used herein refers to a high current draw state where the current over a circuit allows the device to perform its primary energized function.

Optical Zone: as used herein refers to an area of an ophthalmic lens through which a wearer of the ophthalmic lens sees.

Power: as used herein refers to work done or energy transferred per unit of time.

Rechargeable or Re-energizable: as used herein refers to a capability of being restored to a state with higher capacity to do work. Many uses within this invention may relate to the capability of being restored with the ability to flow electrical current at a certain rate and for a certain, reestablished period.

Reenergize or Recharge: as used herein refers to restoring to a state with higher capacity to do work. Many uses within this invention may relate to restoring a device to the capability to flow electrical current at a certain rate and for a certain, reestablished period.

Reference: as use herein refers to a circuit which produces an, ideally, fixed and stable voltage or current output suitable for use in other circuits. A reference may be derived from a bandgap, may be compensated for temperature, supply, and process variation, and may be tailored specifically to a particular application-specific integrated circuit (ASIC).

Reset Function: as used herein refers to a self-triggering algorithmic mechanism to set a circuit to a specific predetermined state, including, for example, logic state or an energization state. A Reset Function may include, for example, a power-on reset circuit, which may work in conjunction with the Switching Mechanism to ensure proper bring-up of the chip, both on initial connection to the power source and on wakeup from Storage Mode.

Sleep Mode or Standby Mode: as used herein refers to a low current draw state of an energized device after the Switching Mechanism has been closed that allows for energy conservation when Operating Mode is not required.

Stacked: as used herein means to place at least two component layers in proximity to each other such that at least a portion of one surface of one of the layers contacts a first surface of a second layer. In some embodiments, a film, whether for adhesion or other functions may reside between the two layers that are in contact with each other through said film.

Stacked Integrated Component Devices or SIC Devices: as used herein refers to the products of packaging technologies that assemble thin layers of substrates that may contain electrical and electromechanical devices into operative-integrated devices by means of stacking at least a portion of each layer upon each other. The layers may comprise component devices of various types, materials, shapes, and sizes. Furthermore, the layers may be made of various device production technologies to fit and assume various contours.

Storage Mode: as used herein refers to a state of a system comprising electronic components where a power source is supplying or is required to supply a minimal designed load current. This term is not interchangeable with Standby Mode.

Substrate Insert: as used herein refers to a formable or rigid substrate capable of supporting an Energy Source within an ophthalmic lens. In some embodiments, the Substrate insert also supports one or more components.

Switching Mechanism: as used herein refers to a component integrated with the circuit providing various levels of resistance that may be responsive to an outside stimulus, which is independent of the ophthalmic device.

Bone conduction devices have been in development since the early 80s, beginning with a sound system that was designed to be worn around the neck like a scarf. The sound system included a radio with speakers that were designed to rest on the user's collar bone and provide the user with sound that was transferred directly from the speakers into the body and to the inner ear. More recently, development of hearing aids and assistive listening devices, headphones, and specialized communication products has increased. These new devices can enable the provision of sound to a user in very noisy environments without blocking outside sound or leakage. Moreover, the devices may be sometimes be used for underwater applications.

Recent developments in Ophthalmic Devices including, for example, contact lenses, have occurred enabling Functionalized Ophthalmic Devices that can be Energized. The Energized Ophthalmic Device can comprise the necessary elements to correct and/or enhance the vision of users using embedded micro-electronics. Additional functionality using micro-electronics can include, for example, variable vision correction, tear fluid analysis, and/or visual feedback to the user. In addition to providing visual functionality, the present disclosure provides for an Ophthalmic Device that includes Micro-Acoustic Elements. The Micro-Acoustic Elements which include an Energized electromechanical system that is capable of converting digital signals into mechanical vibrations in order to deliver sound frequencies to the inner ear. In some embodiments, the Ophthalmic Device can be in wireless communication with one or more wireless device(s) and receive signal data that can be played through the Micro-Acoustic Elements. The wireless device(s) can include, for example, a smart phone device, a tablet, a personal computer, a FOB, an MP3 player, a PDA, and the such.

Referring now to FIG. 1, a diagrammatic representation of a first exemplary energized ophthalmic device comprising both optics and a micro acoustic electromechanical system in accordance with aspects of the present disclosure is depicted. According to some aspects of the present disclosure, the Ophthalmic Device of the present disclosure may be a contact lens 101. The contact lens 101 may be a soft hydrogel lens and can include a silicone containing component. A "silicone-containing component" is one that contains at least one [—Si—O—] unit in a monomer, macromer or prepolymer. Preferably, the total Si and attached O are present in the silicone-containing component in an amount greater than about 20 weight percent, and more preferably greater than 30 weight percent of the total molecular weight of the silicone-containing component. Useful silicone-containing components preferably comprise polymerizable functional groups such as acrylate, methacrylate, acrylamide, methacrylamide, vinyl, N-vinyl lactam, N-vinylamide, and styryl functional groups. Suitable silicone containing components include compounds of:

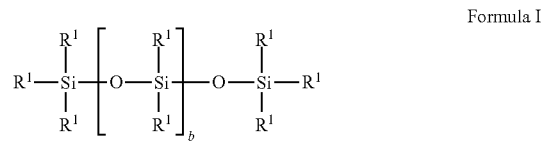

Formula I where $R^1$ is independently selected from monovalent reactive groups, monovalent alkyl groups, or monovalent aryl groups, any of the foregoing which may further comprise functionality selected from hydroxy, amino, oxa, carboxy, alkyl carboxy, alkoxy, amido, carbamate, carbonate, halogen or combinations thereof; and monovalent siloxane chains comprising 1-100 Si—O repeat units which may further comprise functionality selected from alkyl, hydroxy, amino, oxa, carboxy, alkyl carboxy, alkoxy, amido, carbamate, halogen or combinations thereof; where b=0 to 500, where it is understood that when b is other than 0, b is a distribution having a mode equal to a stated value; wherein at least one $R^1$ comprises a monovalent reactive group, and in some embodiments between one and 3 $R^1$ comprise monovalent reactive groups.

As used herein "monovalent reactive groups" are groups that can undergo free radical and/or cationic polymerization. Non-limiting examples of free radical reactive groups include (meth)acrylates, styryls, vinyls, vinyl ethers, C1 6alkyl(meth)acrylates, (meth)acrylamides, $C_{1-6}$ alkyl(meth)acrylamides, N-vinyllactams, N-vinylamides, $C_{2-12}$ alkenyls, $C_{2-12}$ alkenylphenyls, $C_{2-12}$ alkenylnaphthyls, $C_{2-6}$ alkenylphenyl $C_{1-6}$ alkyls, O-vinylcarbamates and O-vinylcarbonates. Non-limiting examples of cationic reactive groups include vinyl ethers or epoxide groups and mixtures thereof. In one embodiment the free radical reactive groups comprises (meth)acrylate, acryloxy, (meth)acrylamide, and mixtures thereof. Suitable monovalent alkyl and aryl groups include unsubstituted monovalent $C_1$ to $C_{16}$ alkyl groups, $C_6$-$C_{14}$ aryl groups, such as substituted and unsubstituted methyl, ethyl, propyl, butyl, 2-hydroxypropyl, propoxypropyl, polyethyleneoxypropyl, combinations thereof and the like.

In one embodiment b is zero, one $R^1$ is a monovalent reactive group, and at least 3 $R^1$ are selected from monovalent alkyl groups having one to 16 carbon atoms, and in another embodiment from monovalent alkyl groups having one to 6 carbon atoms. Non-limiting examples of silicone components of this embodiment include 2-methyl-,2-hydroxy-3-[3-[1,3,3,3-tetramethyl-1-[(trimethylsilyl)oxy]disiloxanyl]propoxy]propyl ester ("SiGMA"), 2-hydroxy-3-methacryloxypropyloxypropyl-tris(trimethylsiloxy) silane, 3-methacryloxypropyltris(trimethylsiloxy) silane ("TRIS"), 3-methacryloxypropylbis(trimethylsiloxy) methylsilane and 3-methacryloxypropylpentamethyl disiloxane.

In another embodiment, b is 2 to 20, 3 to 15 or in some embodiments 3 to 10; at least one terminal $R^1$ comprises a monovalent reactive group and the remaining $R^1$ are selected from monovalent alkyl groups having 1 to 16 carbon atoms, and in another embodiment from monovalent alkyl groups having 1 to 6 carbon atoms. In yet another embodiment, b is 3 to 15, one terminal $R^1$ comprises a monovalent reactive group, the other terminal $R^1$ comprises a monovalent alkyl group having 1 to 6 carbon atoms and the remaining $R^1$ comprise monovalent alkyl group having 1 to 3 carbon atoms. Non-limiting examples of silicone components of this embodiment include (mono-(2-hydroxy-3-methacryloxypropyl)-propyl ether terminated polydimethylsiloxane (400-1000 MW)) ("OH-mPDMS"), monomethacryloxypropyl terminated mono-n-butyl terminated polydimethylsiloxanes (800-1000 MW), ("mPDMS"). In another embodiment b is 5 to 400 or from 10 to 300, both terminal $R^1$ comprise monovalent reactive groups and the remaining $R^1$ are independently selected from monovalent alkyl groups having 1 to 18 carbon atoms which may have ether linkages between carbon atoms and may further comprise halogen.

In one embodiment, where a silicone hydrogel lens is desired, the lens of the present disclosure will be made from a reactive mixture comprising at least about 20 and preferably between about 20 and 70% wt silicone containing components based on total weight of reactive monomer components from which the polymer is made. In another embodiment, one to four $R^1$ comprises a vinyl carbonate or carbamate of the formula:

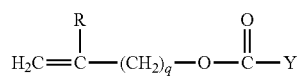

Formula II wherein: Y denotes O—, S— or NH—; R denotes, hydrogen or methyl; d is 1, 2, 3 or 4; and q is 0 or 1.

The silicone-containing vinyl carbonate or vinyl carbamate monomers specifically include: 1,3-bis[4-(vinyloxycarbonyloxy)but-1-yl]tetramethyl-disiloxane; 3-(vinyloxycarbonylthio) propyl-[tris(trimethylsiloxy)silane]; 3-[tris(trimethylsiloxy)silyl]propyl allyl carbamate; 3-[tris(trimethylsiloxy)silyl]propyl vinyl carbamate; trimethylsilylethyl vinyl carbonate; trimethylsilylmethyl vinyl carbonate, and

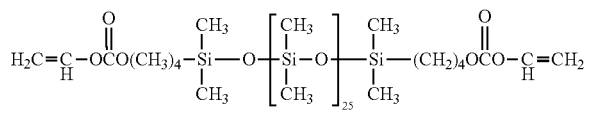

where biomedical devices with modulus below about 200 are desired, only one $R^1$ shall comprise a monovalent reactive group and no more than two of the remaining $R^1$ groups will comprise monovalent siloxane groups.

Another class of silicone-containing components includes polyurethane macromers of the following formulae:

Formula IV-VI wherein: D denotes an alkyl diradical, an alkyl cycloalkyl diradical, a cycloalkyl diradical, an aryl diradical or an alkylaryl diradical having 6 to 30 carbon atoms, G denotes an alkyl diradical, a cycloalkyl diradical, an alkyl cycloalkyl diradical, an aryl diradical or an alkylaryl diradical having 1 to 40 carbon atoms and which may contain ether, thio or amine linkages in the main chain; * denotes a urethane or ureido linkage; $_a$ is at least 1; A denotes a divalent polymeric radical of formula:

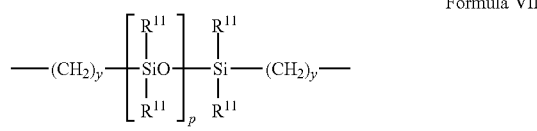

Formula VII $R^{11}$ independently denotes an alkyl or fluoro-substituted alkyl group having 1 to 10 carbon atoms which may contain ether linkages between carbon atoms; y is at least 1; and p provides a moiety weight of 400 to 10,000; each of E and $E^1$ independently denotes a polymerizable unsaturated organic radical represented by formula:

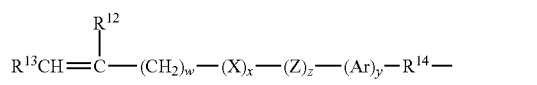

Formula VIII wherein: $R^{12}$ is hydrogen or methyl; $R^{13}$ is hydrogen, an alkyl radical having 1 to 6 carbon atoms, or a —CO—Y—$R^{15}$ radical wherein Y is —O—, Y—S— or —NH—; $R^{14}$ is a divalent radical having 1 to 12 carbon atoms; X denotes —CO— or —OCO—; Z denotes —O— or —NH—; Ar denotes an aromatic radical having 6 to 30 carbon atoms; w is 0 to 6; x is 0 or 1; y is 0 or 1; and z is 0 or 1. A preferred silicone-containing component is a polyurethane macromer represented by the following formula:

Formula IX

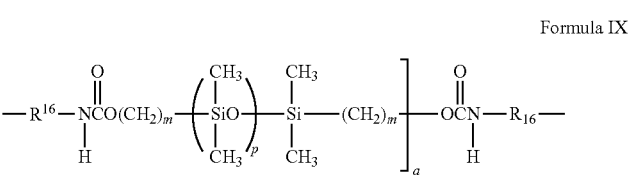

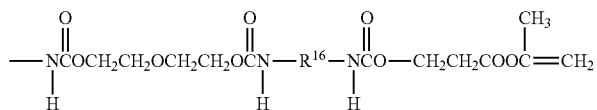

wherein R[16] is a diradical of a diisocyanate after removal of the isocyanate group, such as the diradical of isophorone diisocyanate. Another suitable silicone containing macromer is compound of formula X (in which x+y is a number in the range of 10 to 30) formed by the reaction of fluoroether, hydroxy-terminated polydimethylsiloxane, isophorone diisocyanate and isocyanatoethylmethacrylate.

depicted. The Media Insert 200 may comprise an Optical Zone 220 that may or may not be functional to provide vision correction. Where the energized function of the ophthalmic device is unrelated to vision, the Optic Zone 220 of the Media Insert 200 may be void of material. In some embodiments, the Media Insert 200 may include a portion not in the Optical Zone 220 comprising a substrate 215 incorporated with ener- Formula X

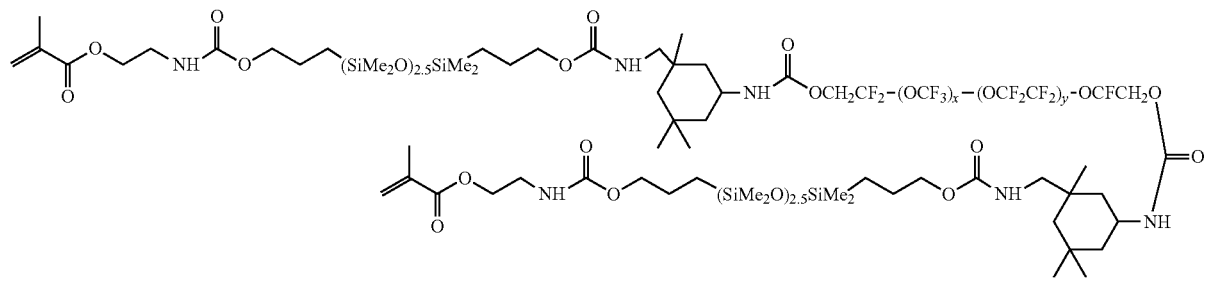

Other silicone containing components suitable for use in this disclosure include macromers containing polysiloxane, polyalkylene ether, diisocyanate, polyfluorinated hydrocarbon, polyfluorinated ether and polysaccharide groups; polysiloxanes with a polar fluorinated graft or side group having a hydrogen atom attached to a terminal difluoro-substituted carbon atom; hydrophilic siloxanyl methacrylates containing ether and siloxanyl linkanges and crosslinkable monomers containing polyether and polysiloxanyl groups. Any of the foregoing polysiloxanes can also be used as the silicone containing component in this disclosure.

The Optical Zone 102 includes that portion of the Ophthalmic Lens 101 providing line of sight for a wearer of the Ophthalmic Device 101. Micro-acoustic element 110 can be located on the peripheral zone outside of an Optic Zone 102, such that the device does not interfere with the user's sight. The micro-acoustic element 110 of the present exemplary embodiment may be powered through an external means. For example, the power may be received using an antenna receiving RF signals that is in communication with a piezoelectric vibration source. The piezoelectric vibration source may form part of, for example, a MEMS acoustic system on a silicon chip with integrated circuits and can include a processor capable of receiving electrical signals and converting them into mechanical vibrations with a frequency from approximately 20 Hz to 20,000 Hz (20 kHz). The piezoelectric source may be encapsulated by one or more film layers including, for example, biomedical compatible packaging materials for implantable micro-systems MDX 42210, FP 4450 and Parylene-C. In some embodiments, the packaged Micro-Acoustic Element 110 may further be encapsulated in the hydrogel material or placed onto a surface of the hydrogel portion of the Ophthalmic Device 101. Although the Micro-Acoustic Element can be encapsulated, vibrational frequencies are able to travel to the orb of the eye and to the inner ear through bone conduction without affecting the user's vision.

Figure 2:
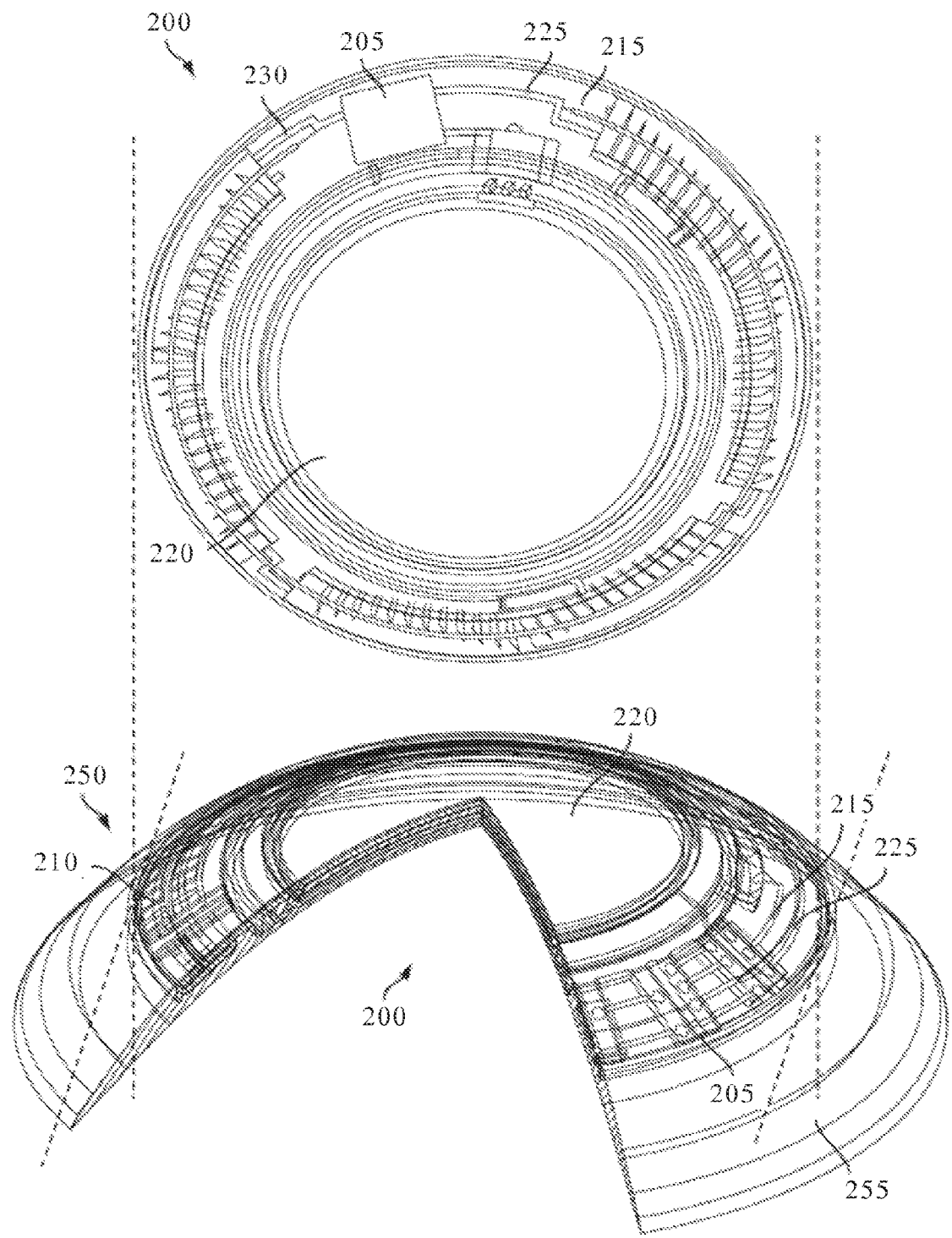
FIG. 2 is a diagrammatic representation of a second exemplary energized ophthalmic device comprising both optics and a micro acoustic electromechanical system in accordance with aspects of the present disclosure.

Referring now to FIG. 2, a diagrammatic representation of a second exemplary Energized Ophthalmic Device 250 comprising both optics and a micro acoustic electromechanical system in accordance with aspects of the present disclosure is depicted. A top view of an exemplary Media Insert 200 for an Energized Ophthalmic Device 250 that can include Micro-Acoustic Elements 205 and an isometric exemplary energized Ophthalmic Device 250 including the Media Insert 200 are gization elements 110 and electronic components 205 which include Micro-Acoustic Elements.

In some embodiments, a power source 210, which may be, for example, a battery, and a load 205, which may be, for example, a semiconductor die, may be attached to the substrate 215. Conductive traces 225 and 230 may electrically interconnect the electronic components 205 and the energization elements 210. In some embodiments, the Media Insert 200 can be fully encapsulated to protect and contain the energization elements 210, traces 225 and 230, and electronic components 205. In some embodiments, the encapsulating material may be semi-permeable, for example, to prevent specific substances, such as water, from entering the Media Insert 100 and to allow specific substances, such as ambient gasses, fluid samples, and/or the byproducts of reactions within energization elements 210, to penetrate and/or escape from the Media Insert 200.

The Media Insert 200 may be included in/or on an Ophthalmic Device 250, which may also comprise a polymeric biocompatible material. The Ophthalmic Device 250 may include a rigid center, soft skirt design wherein a central rigid optical element comprises the Media Insert 200. In some specific embodiments, the Media Insert 200 may be in direct contact with the atmosphere and/or the corneal surface on respective anterior and posterior surfaces, or alternatively, the Media Insert 200 may be encapsulated in the Ophthalmic Device 250. The periphery 255 of the Ophthalmic Device 250 may be a soft skirt material, including, for example, a hydrogel material. The infrastructure of the Media Insert 200 and the Ophthalmic Device 250 can provide an environment to perform analysis of ocular fluid while in contact with an ocular surface according to aspects of the present invention. Ocular fluid samples can include any one, or a combination of: tear fluid, aqueous humour, vitreous humour, and other interstitial fluids located in the eye. In addition, in the present exemplary Ophthalmic Device 250, the Micro-Acoustic Elements may be placed inside or on a surface of the media insert 200. In some embodiments, the audible signals transmitted to the user using the Micro-Acoustic Elements may be related to the fluid analysis of ocular fluid. For example, the audible signal may be a recommended action and/or warning based on levels of biomarkers measured on a tear fluid sample.

Figure 3:
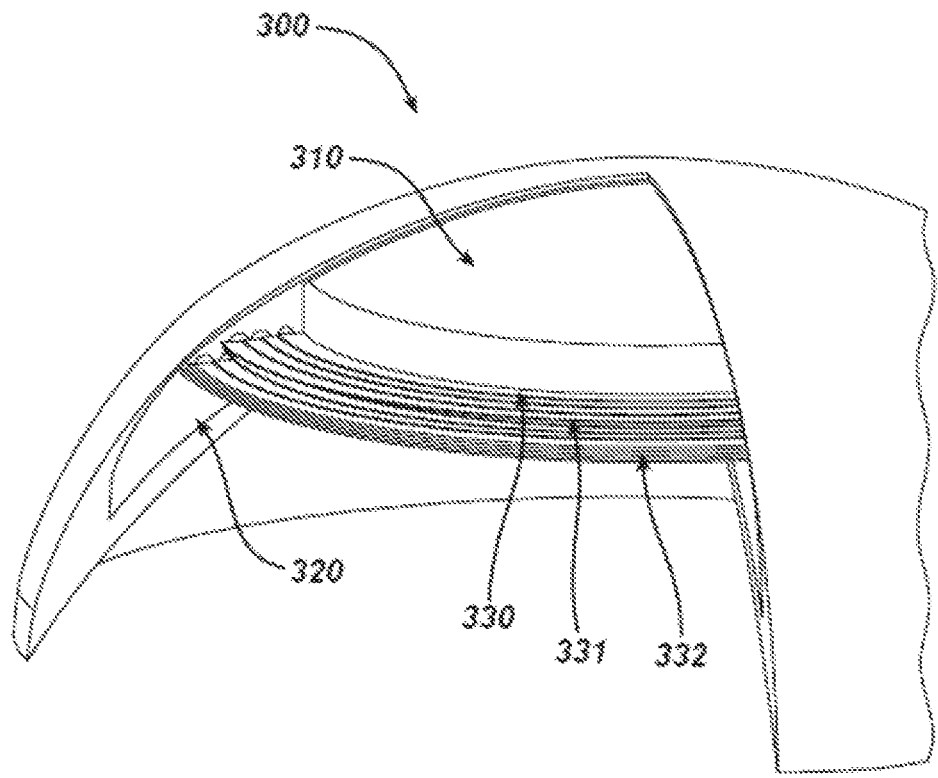
FIG. 3 is a diagrammatic representation of a third exemplary energized ophthalmic device comprising both optics and a micro acoustic electromechanical system in accordance with aspects of the present disclosure.

Referring now to FIG. 3, a diagrammatic representation of a third exemplary energized ophthalmic device comprising both optics and a micro-acoustic electromechanical system in accordance with aspects of the present disclosure is depicted. In particular, a three dimensional cross section representation of an exemplary Ophthalmic Lens 300 including a Functionalized Layer Media Insert 320 configured to include Micro-Acoustic Elements on one or more of its layers 330, 331, 332 is illustrated. In the present exemplary embodiment, the Media Insert 320 surrounds the entire periphery of the Ophthalmic Lens 300. One skilled in the art can understand that the actual Media Insert 320 may comprise a full annular ring or other shapes that still may reside inside or on the hydrogel portion of the Ophthalmic lens 300 and be within the size and geometry constraints presented by the ophthalmic environment of the user.

Layers 330, 331 and 332 are meant to illustrate three of numerous layers that may be found in a Media Insert 320 formed as a stack of functional layers. In some embodiments, for example, a single layer may include one or more of: active and passive components and portions with structural, electrical or physical properties conducive to a particular purpose including the Communication System functions described in the present disclosure. Furthermore, in some embodiments, a layer 330 may include an Energy Source, such as, one or more of: a battery, a capacitor and a receiver within the layer 330. Item 331 then, in a non-limiting exemplary sense may comprise microcircuitry in a layer that detects actuation signals for the Ophthalmic Lens 300. In some embodiments, a power regulation layer 332, may be included that is capable of receiving power from external sources, charges the battery layer 330 and controls the use of battery power from layer 330 when the Ophthalmic Lens 300 is not in a charging environment. The power regulation may also control signals to an exemplary active lens, demonstrated as item 310 in the center annular cutout of the Media Insert 320.

An energized lens with an embedded Media Insert 320 may include an energy source, such as an electrochemical cell or battery as the storage means for the energy and in some embodiments, encapsulation, and isolation of the materials comprising the energy source from an environment into which an Ophthalmic Lens is placed. In some embodiments, a Media Insert 320 can also include a pattern of circuitry, components, and energy sources. Various embodiments may include the Media Insert 320 locating the pattern of circuitry, components and Energy Sources around a periphery of an Optic Zone through which a wearer of an Ophthalmic Lens would see, while other embodiments may include a pattern of circuitry, components and Energy Sources which are small enough to not adversely affect the sight of the Ophthalmic Lens wearer and therefore the Media Insert 320 may locate them within, or exterior to, an Optical Zone.

Reference has been made to electronic circuits making up part of the componentry of Ophthalmic Devices incorporating Micro-Acoustic Elements. In some embodiments according to aspects of the disclosure, a single and/or multiple discrete electronic devices may be included as discrete chips, for example, in the ophthalmic Media Inserts. In other embodiments, the energized electronic elements can be included in the Media Insert in the form of Stacked Integrated Components. Accordingly and referring now to FIG. 4, a schematic diagram of an exemplary cross section of a Stacked Integrated Component implementing micro-acoustic elements incorporated within Ophthalmic Devices is depicted. In particular, the Media Insert may include numerous layers of different types which are encapsulated into contours consistent with the ophthalmic environment that they will occupy. In some embodiments, these Media Inserts with Stacked Integrated Component layers may assume the entire annular shape of the Media Insert. Alternatively in some cases, the Media Insert may be an annulus whereas the Stacked Integrated Component may occupy just a portion of the volume within the entire shape.

Figure 4:
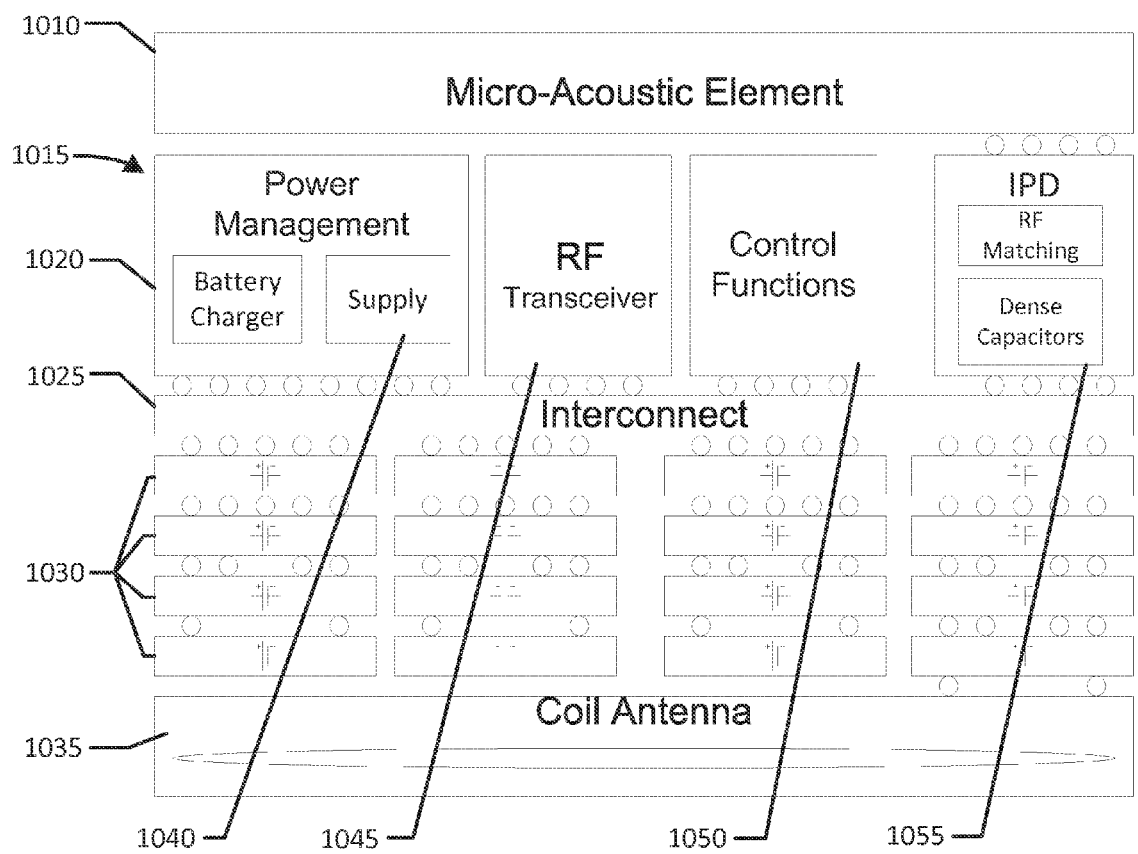
FIG. 4 is a schematic diagram of an exemplary cross section of a stacked die integrated component implementing a micro acoustic electromechanical system in accordance with aspects of the present disclosure.

As shown in FIG. 4, there may be thin film batteries 1030 used to provide energization. In some embodiments, these thin film batteries 1030 may comprise one or more of the layers that can be stacked upon each other with multiple components in the layers and interconnections therebetween.

In some embodiments, there may be additional interconnections between two layers that are stacked upon each other. In the state of the art there may be numerous manners to make these interconnections; however, as demonstrated the interconnection may be made through solder ball interconnections between the layers. In some embodiments only these connections may be required; however, in other cases the solder balls may contact other interconnection elements, as for example with a component having through layer vias.

In other layers of the Stacked Integrated Component Media Insert, a layer 1025 may be dedicated for the interconnections two or more of the various components in the interconnect layers. The interconnect layer 1025 may contain, vias and routing lines that can pass signals from various components to others. For example, interconnect layer 1025 may provide the various battery elements connections to a power management unit 1020 that may be present in a technology layer 1015. Other components in the technology layer 1015 can include, for example, a transceiver 1045, control components 1050 and the like. In addition, the interconnect layer 1025 may function to make connections between components in the technology layer 1015 as well as components outside the technology layer 1015; as may exist for example in the Integrated Passive Device 1055. There may be numerous manners for routing of electrical signals that may be supported by the presence of dedicated interconnect layers such as interconnect layer 1025.

In some embodiments, the technology layer 1015, like other layer components, may be included as multiple layers as these features represent a diversity of technology options that may be included in Media Inserts. In some embodiments, one of the layers may include CMOS, BiCMOS, Bipolar, or memory based technologies whereas the other layer may include a different technology. Alternatively, the two layers may represent different technology families within a same overall family; as for example one layer may include electronic elements produced using a 0.5 micron CMOS technology and another layer may include elements produced using a 20 nanometer CMOS technology. It may be apparent that many other combinations of various electronic technology types would be consistent within the art described herein.

In some embodiments, the Media Insert may include locations for electrical interconnections to components outside the insert. In other examples, however, the Media Insert may also include an interconnection to external components in a wireless manner. In such cases, the use of antennas in an antenna layer 1035 may provide exemplary manners of wireless communication. In many cases, such an antenna layer 1035 may be located, for example, on the top or bottom of the stacked integrated component device within the Media Insert.

In some of the embodiments discussed herein, the battery elements 1030 may be included as elements in at least one of the stacked layers themselves. It may be noted as well that other embodiments may be possible where the battery elements 1030 are located externally to the stacked integrated component layers. Still further diversity in embodiments may derive from the fact that a separate battery or other energization component may also exist within the Media Insert, or alternatively these separate energization components may also be located externally to the Media Insert.

Micro-Acoustic Element(s) 1010 may be included in a Stacked Integrated Component architecture. In some embodiments, the Micro-Acoustic Element 1010 components may be attached as a portion of a layer. In other embodiments, the entire Micro-Acoustic Element 1010 may also comprise a similarly shaped component as the other Stacked Integrated Components.

Figure 5:
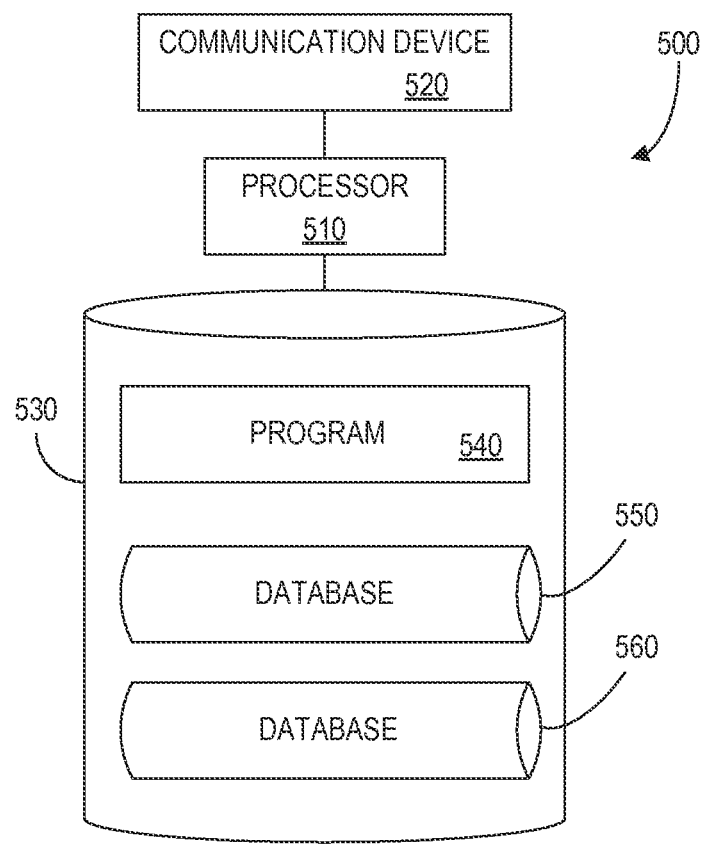
FIG. 5 is a schematic diagram of a processor that may be used to implement some aspects of the present disclosure.

Referring now to FIG. 5 a controller 500 that may be used in embodiments of the present disclosure is illustrated. The controller 500 can include one or more processors 510, which may include one or more processor components coupled to a communication device 520. In some embodiments, a controller 500 can be used to transmit energy to the Energy Source placed in the Ophthalmic Lens.

The processors 510 are coupled to a communication device configured to communicate energy via a communication channel. The communication device may be used to electronically communicate with components within the Media Insert, for example. The communication device 520 may also be used to communicate, for example, with one or more controller apparatus or programming/interface device components.

The processor 510 is also in communication with a storage device 530. The storage device 530 may comprise any appropriate information storage device, including combinations of magnetic storage devices, optical storage devices, and/or semiconductor memory devices such as Random Access Memory (RAM) devices and Read Only Memory (ROM) devices.

The storage device 530 can store a program 540 for controlling the processor 510. The processor 510 performs instructions of a software program 540, and thereby operates in accordance with the present invention. For example, the processor 510 may receive information descriptive of Media Insert placement, component placement, and the like. The storage device 530 can also store ophthalmic related data in one or more databases 550 and 560. The database may include, for example, predetermined ocular fluid sample measurement thresholds, metrology data, pre-recorded sound signals, and specific control sequences for controlling energy to and from a Media Insert. The database may also include parameters and controlling algorithms for the control of the Micro-Acoustic Elements that may reside in the ophthalmic device as well as data and/or measured feedback that can result from their action. In some embodiments, that data may be ultimately communicated to an external reception device.

Figure 6:
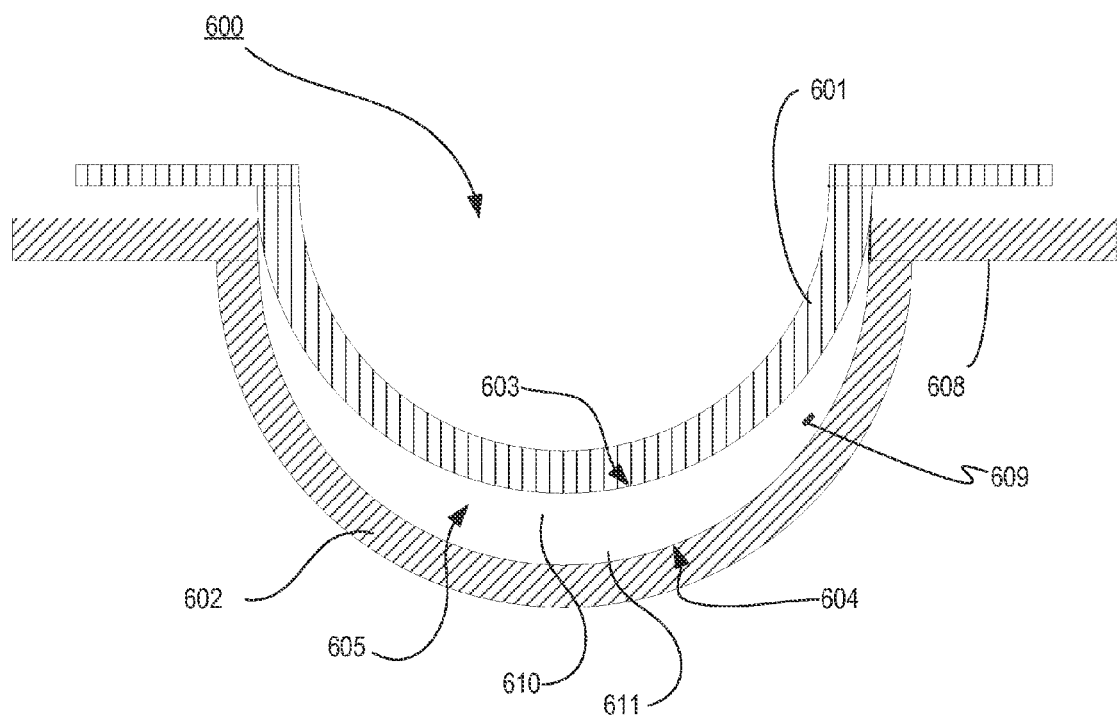
FIG. 6 is a schematic diagram of an exemplary Mold for an Ophthalmic Device with Micro-Acoustic Elements according to some aspects of the present disclosure.

Referring now to FIG. 6, a diagram of an exemplary Mold for an Ophthalmic Lens with Micro-Acoustic Element(s) 609 is illustrated. As used herein, the term Mold can include a mold assembly 600 having a cavity 605 into which a Lens forming mixture 610 can be dispensed such that upon reaction or cure of the Lens Forming Mixture, an Ophthalmic Lens of a desired shape is produced. In some embodiments, the Molds and mold assemblies 600 may be made up of more than one "mold parts" or "mold pieces" 601-602. For example, the mold parts 601-602 can be brought together such that a cavity 605 is formed between the mold parts 601-602 in which a lens can be formed. This combination of mold parts 601-602 is preferably temporary. Upon formation of the Ophthalmic Lens, the mold parts 601-602 can again be separated and the Ophthalmic Lens can be Released from a Mold.

At least one mold part 601-602 has at least a portion of its Lens Forming Surface 603-604 in contact with the Lens Forming Mixture such that upon reaction or cure of the Lens Forming Mixture 610 that surface 603-604 provides a desired shape and form to the portion of the Ophthalmic Lens with which it is in contact. The same may be true of at least one other mold part 601-602.

Thus, for example, in one preferred embodiment a mold assembly 600 can be formed from two parts 601-602, a female concave piece (front piece) 602 and a male convex piece (back piece) 601 with a cavity formed between them. The portion of the concave surface 604 which can make contact with Lens Forming Mixture 610 has the curvature of the front curve of an Ophthalmic Lens to be produced in the mold assembly 600 and is sufficiently smooth and formed such that the surface of an Ophthalmic Lens formed by polymerization of the Lens Forming Mixture which is in contact with the concave surface 604 is optically acceptable.

In some embodiments, the front mold piece 602 can also have an annular flange integral with and surrounding circular circumferential edge 608 and extends from it in a plane normal to the axis and extending from the flange (not shown).

A Lens Forming Surface can include a surface 603-604 with an optical quality surface finish, which indicates that it is sufficiently smooth and formed so that an Ophthalmic Lens surface fashioned by the polymerization of a Lens Forming Mixture in contact with the molding surface is optically acceptable. Further, in some embodiments, the Lens Forming Surface 603-604 can have a geometry that may be necessary to impart to the lens surface the desired optical characteristics, including without limitation, spherical, aspherical and cylinder power, wave front aberration correction, corneal topography correction and the like as well as any combinations thereof.

Mold part 601-602 material can include a polyolefin of one or more of: polypropylene, polystyrene, polyethylene, polymethyl methacrylate, and modified polyolefins. A preferred alicyclic co-polymer contains two different alicyclic polymers and is sold by Zeon Chemicals L.P. under the trade name ZEONOR. There are several different grades of ZEONOR. Various grades may have glass transition temperatures ranging from 105 C to 160 C. A specifically preferred material is ZEONOR 1060R. Other Mold materials that may be combined with one or more additives to form an Ophthalmic Lens Mold include, for example, Zieglar-Natta polypropylene resins (sometimes referred to as znPP). On exemplary Zieglar-Natta polypropylene resin is available under the name PP 9544 MED. PP 9544 MED is a clarified random copolymer for clean molding as per FDA regulation 21 CFR (c)3.2 made available by ExxonMobile Chemical Company. PP 9544 MED is a random copolymer (znPP) with ethylene group (hereinafter 9544 MED). Other exemplary Zieglar-Natta polypropylene resins include: Atofina Polypropylene 3761 and Atofina Polypropylene 3620WZ. Still further, in some embodiments, the Molds of the disclosure may contain polymers such as polypropylene, polyethylene, polystyrene, polymethyl methacrylate, modified polyolefins containing an alicyclic moiety in the main chain and cyclic polyolefins. This blend can be used on either or more Mold parts, for example, where it is preferred that this blend is used on the back curve and the front curve consists of the alicyclic co-polymers.

In some preferred methods of making Molds 600, injection molding can be utilized according to known techniques, however, embodiments can also include Molds fashioned by other techniques including, for example: lathing, diamond turning, or laser cutting. Typically, lenses are formed on at least one surface of both Mold parts 601-602. However, in some embodiments, one surface of an Ophthalmic Lens may be formed from a Mold part 601-602 and another surface of a lens can be free-formed as described by other methods.

Figure 7:
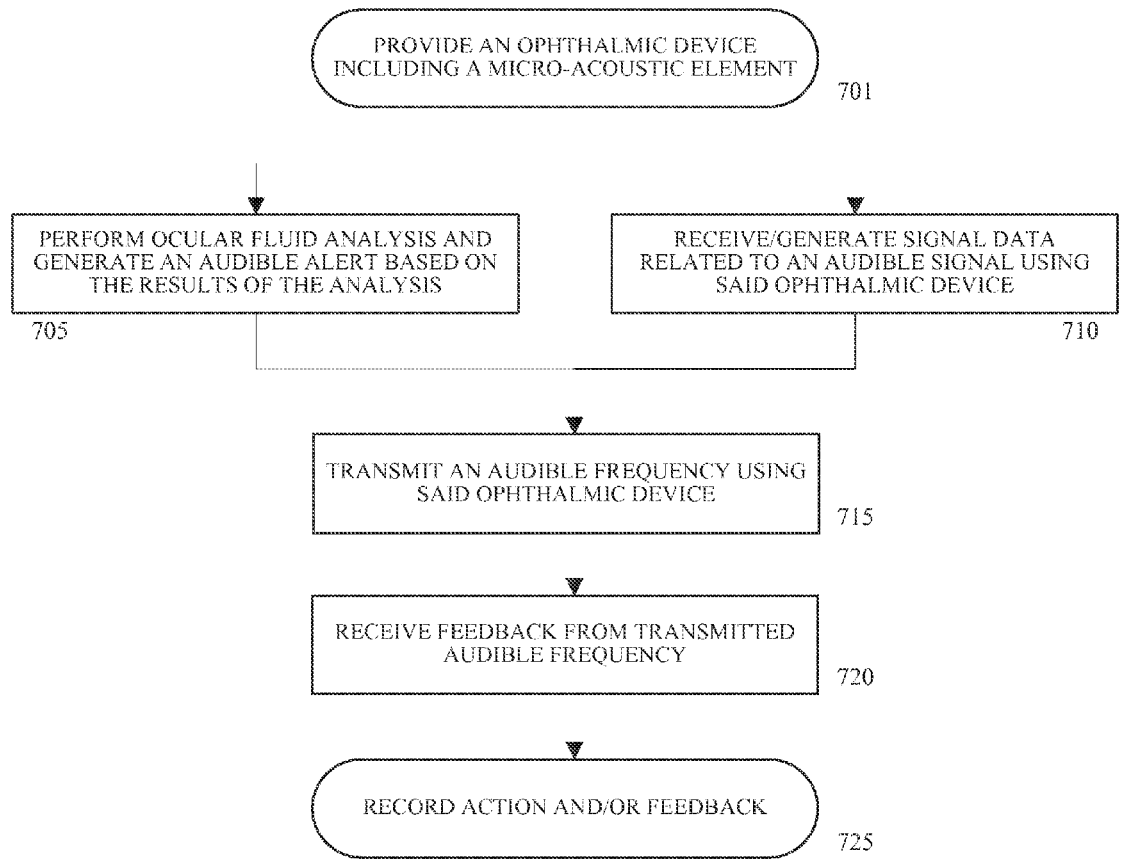
FIG. 7 illustrates exemplary method steps that may be used to implement the micro-acoustic element(s) of the ophthalmic device according to aspects of the present disclosure.

Referring now to FIG. 7, exemplary method steps that may be used to implement the micro-acoustic element(s) of the ophthalmic device according to aspects of the present disclosure are illustrated. Beginning at step 701, an ophthalmic device including a micro-acoustic element(s) is provided to a user. In some embodiments, the ophthalmic device may include two contact lenses configured to include micro-acoustic elements, in addition to providing vision correction and/or enhancement.

At step 705, in some embodiments also including microfluidic elements capable of measuring biomarker concentrations in tear fluid samples, an audible alert can be generated based on the results of an ocular fluid sample analysis. For example, a warning and/or alert may be played to the user when the levels of particular biomarkers are above/below a pre-determined threshold. Concentration changes of biomarkers can be monitored using the one or more sensors. The monitoring of the biomarkers may occur at a predetermined frequency or upon demand through a user interface and/or an activation sensor in the ophthalmic device. Biomarkers can include, for example, those correlated to glucose levels, depression, and blood pressure. The audible alert may include a message to the wearer indicating that an action is desired, for example, that a medication needs to be taken or suspended.

At step 710, signal data related to a surrounding environmental condition, location, proximity to an associated device, received message, and the such, may be received by a communication device of the ophthalmic device. In some embodiments, the signal data may be received from an exterior processor including for example, a processor of a wireless device, personal computer, etc., and transmitted to the user through an audible signal that can be heard by the user. The audible signal may be played in conjunction with a visual signal, e.g., as part of a video clip. Transmission of information can occur wirelessly, for example, via an RF frequency, a local area network (LAN), and/or a private area network (PAN), depending on the communication device and functionality implemented in the ophthalmic device. Moreover, in some embodiments the audible signal may be generated using sensor data from one or more sensor(s) in the ophthalmic device.

At step 715, the audible frequency may be transmitted to the user using the micro-acoustic element of the ophthalmic device. The frequency can be conducted from the ocular orb region to the inner ear through bone conduction using the ophthalmic device. Accordingly, at step 720, from the audible frequency transmitted to the user, the user can actively provide feedback using an associated device, a sensor within the ophthalmic device, or from an involuntary response captured by a sensor within the lens. For example, an active response may include silencing the message using an associate device's interface, while an involuntary response may include a blink or a sensed brain emitted frequency. At step 725, the audible frequency provided to the user and/or the feedback from the user can be recorded. The records may be maintained as part of a user's history, to prevent sending duplicate messages, and/or for prioritization of future message, for example.

The many features and advantages of the invention are apparent from the detailed specification, and thus, it is intended by the appended claims to cover all such features and advantages of the invention which fall within the true spirit and scope of the invention. Further, because numerous modifications and variations will readily occur to those skilled in the art, it is not desired to limit the invention to the exact construction and operation illustrated and described, and accordingly, all suitable modifications and equivalents may be resorted to, falling within the scope of the invention.

The invention claimed is:

1. An ophthalmic lens, comprising:
an energy source; a microprocessor in communication with and energized by the energy source; and a micro-electromechanical transducer also energized by the said energy source and in electrical communication with the microprocessor, wherein the microprocessor is configured to convert electrical signals into mechanical vibrations for the micro-electromechanical transducer to provide an audible signal to a user of the ophthalmic lens.

2. The ophthalmic device of claim 1, wherein the ophthalmic lens is a hydrogel contact lens.

3. The ophthalmic lens of claim 1, additionally comprising:
an antenna configured to provide a wireless communication between the microprocessor of the ophthalmic lens and a wireless device.

4. The ophthalmic lens of claim 3, wherein the antenna is configured to receive an RF signal used to energize the ophthalmic lens.

5. The ophthalmic lens of claim 3, wherein the wireless device in wireless communication with the microprocessor of the ophthalmic lens is one or more of a smart phone, a tablet, a personal computer, a MP3 player, a medicinal pump, and a personal digital assistant.

6. The ophthalmic lens of claim 5, wherein the audible signal is a message received from one or more of the wireless devices in wireless communication with the ophthalmic lens.

7. The ophthalmic lens of claim 1, additionally comprising:
one or more sensor(s) in communication with the microprocessor of the ophthalmic lens.

8. The ophthalmic lens of claim 7, wherein the one or more sensor(s) are configured to monitor a location of the user and the audible signal includes information related to said location of the user.

9. The ophthalmic lens of claim 7, additionally comprising:
micro-fluidic elements configured to provide ocular fluid samples to the one or more sensors.

10. The ophthalmic lens of claim 9, wherein the sensors are configured to monitor concentration levels of biomarkers in an ocular fluid sample and the audible signal is generated according to the concentration levels of biomarkers in said ocular fluid sample.

11. The ophthalmic lens of claim 1, wherein the audible signal is generated with a frequency from about 20 Hz to 20,000 Hz (20 kHz).

12. The ophthalmic lens of claim 1, wherein the audible signal is a message alert informing the user of an emergency medical condition.

13. The ophthalmic lens of claim 1, wherein the energy source, the micro-electromechanical transducer and the microprocessor are configured as stacked integrated component devices.

14. A method of transmitting an audible signal to a user, comprising:
receiving digital signal data through a wireless communication element of an energized ophthalmic lens; and
converting said signal data transmitted through the wireless communication element into mechanical vibrations producing an audible signal using a processor and a micro-electromechanical transducer that form part of the energized ophthalmic lens.

15. The method of claim 14, additionally comprising:
generating feedback data from the user's response to the audible signal to be transmitted to the wireless device.

16. The method of claim 14, additionally comprising:
recording an audible signal's output in a database.

17. The method of claim 14, wherein the digital data is received from a wireless device configured to form a wireless connection with the ophthalmic lens.

18. A method of transmitting an audible signal to a user, comprising:
- generating signal data using one or more sensor(s) that form part of an ophthalmic lens;
- transmitting said generated signal data to a processor; and
- converting, using the processor and a micro-electromechanical transducer that form part of the ophthalmic lens, said transmitted signal into an audible signal for the user of the ophthalmic lens.

19. The method of claim 18, additionally comprising:
generating feedback data from the user's response to the audible signal.

20. The method of claim 18, additionally comprising:
recording an audible signal's output in a database.

* * * * *